US011065191B2

United States Patent
Souzy et al.

(10) Patent No.: US 11,065,191 B2
(45) Date of Patent: Jul. 20, 2021

(54) METHOD FOR THICKENING A COSMETIC FORMULATION USING AN ALKALI SWELLABLE EMULSION OF A POLYMER WITH AMPS AND WHICH IS RICH IN ACRYLIC ACID

(71) Applicant: COATEX, Genay (FR)

(72) Inventors: Renaud Souzy, Caluire et Cuire (FR); Jean-Marc Suau, Lucenay (FR); Yves Kensicher, Theize (FR); Olivier Guerret, Pern (FR)

(73) Assignee: COATEX, Genay (FR)

( * ) Notice: Subject to any disclaimer, the term of this patent is extended or adjusted under 35 U.S.C. 154(b) by 160 days.

(21) Appl. No.: 15/291,504

(22) Filed: Oct. 12, 2016

(65) Prior Publication Data

US 2017/0027846 A1 Feb. 2, 2017

Related U.S. Application Data

(60) Division of application No. 14/141,760, filed on Dec. 27, 2013, now abandoned, which is a continuation of application No. 13/411,809, filed on Mar. 5, 2012, now Pat. No. 8,642,056.

(60) Provisional application No. 61/452,733, filed on Mar. 15, 2011.

(30) Foreign Application Priority Data

Mar. 7, 2011 (FR) .................................... 1151812

(51) Int. Cl.
| | |
|---|---|
| *A61K 8/81* | (2006.01) |
| *A61Q 19/00* | (2006.01) |
| *A61K 8/06* | (2006.01) |
| *C08F 220/58* | (2006.01) |
| *C08F 220/28* | (2006.01) |
| *C08F 220/06* | (2006.01) |
| *C08F 220/12* | (2006.01) |

(52) U.S. Cl.
CPC .............. *A61K 8/8158* (2013.01); *A61K 8/06* (2013.01); *A61K 8/068* (2013.01); *A61K 8/8147* (2013.01); *A61Q 19/00* (2013.01); *C08F 220/06* (2013.01); *C08F 220/12* (2013.01); *C08F 220/28* (2013.01); *C08F 220/58* (2013.01); *A61K 2800/10* (2013.01); *A61K 2800/33* (2013.01); *A61K 2800/48* (2013.01); *A61K 2800/546* (2013.01)

(58) Field of Classification Search
None
See application file for complete search history.

(56) References Cited

U.S. PATENT DOCUMENTS

| | | | |
|---|---|---|---|
| 2,118,566 | A | 5/1938 | De Wayne Miles |
| 4,384,096 | A | 5/1983 | Sonnabend |
| 4,499,002 | A | 2/1985 | Masler, III et al. |
| 6,063,857 | A | 5/2000 | Greenblatt et al. |
| 6,465,402 | B1 | 10/2002 | Lorant |
| 6,897,253 | B2 | 5/2005 | Schmucker-Castner et al. |
| 2003/0082220 | A1 | 5/2003 | Nakayama |
| 2009/0305934 | A1 | 12/2009 | Creamer et al. |
| 2010/0247473 | A1 | 9/2010 | Blondel |
| 2010/0292347 | A1 | 11/2010 | Kensicher et al. |

FOREIGN PATENT DOCUMENTS

| | | |
|---|---|---|
| EP | 1 055 406 A2 | 11/2000 |
| FR | 2 905 595 A1 | 3/2008 |
| WO | WO 2007/144721 | 12/2007 |
| WO | 2008/107034 A2 | 9/2008 |

OTHER PUBLICATIONS

International Search Report dated Jun. 8, 2012 in PCT/IB2011/003126 (with English translation of Category of Cited Documents).
Rieger, et al., Surfactants in Cosmetics $2^{nd}$ edition, 1997, https://books.google.com/books?hl=en&id=2DcyKqj6dDsC&oi=fnd&pg=PR1&dq=sufactants+in+cosmetics&ots=Dq5Jgfqkao&sig=KaxqqpjuzgzF5e1PhTGz8slyi9s#v=onepage&q=surfactants%20in%20cosmetics&f=false.

*Primary Examiner* — Jennifer A Berrios
(74) *Attorney, Agent, or Firm* — Oblon, McClelland, Maier & Neustadt, L.L.P.

(57) ABSTRACT

Process for thickening a composition, through the use of a direct emulsion in water, which is alkali-swellable, of a polymer of the ASE or HASE type, which is both rich in acrylic acid and which has a certain quantity of AMPS. The use of such emulsions simultaneously allows there to be no obligation to use surfactants and organic solvents other than water, and allows the thickening phenomenon to be activated for pHs of less than 7: this latter characteristic is particularly advantageous for formulations intended to be used in contact with skin.

20 Claims, 1 Drawing Sheet

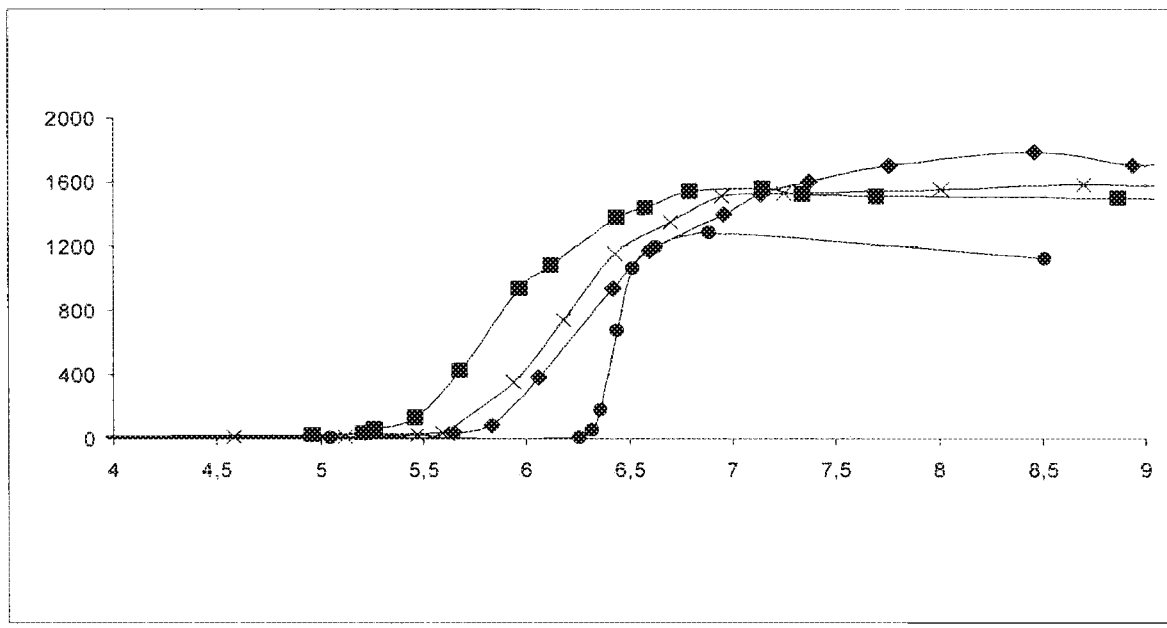

METHOD FOR THICKENING A COSMETIC FORMULATION USING AN ALKALI SWELLABLE EMULSION OF A POLYMER WITH AMPS AND WHICH IS RICH IN ACRYLIC ACID

REFERENCE TO PRIOR APPLICATION

This application is a divisional of application Ser. No. 14/141,760, filed on Dec. 27, 2013, which is a continuation of application Ser. No. 13/411,809 filed Mar. 5, 2012, and claims priority to U.S. provisional application Ser. No. 61/452,733, filed Mar. 15, 2011 and incorporated herein by reference; and to French patent application 11 51812, filed Mar. 7, 2011, both and incorporated herein by reference.

FIELD OF THE INVENTION

The present invention concerns a process for thickening a composition, preferably a cosmetic composition, through the use of a direct emulsion in water, which is alkali-swellable, of a polymer of the ASE or HASE type, which is both rich in acrylic acid and which has a certain quantity of AMPS. The use of such emulsions simultaneously allows there to be no obligation to use surfactants and organic solvents other than water, and allows the thickening phenomenon to be activated for pHs of less than 7: this latter characteristic is particularly advantageous for formulations intended to be used in contact with human skin.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

DISCUSSION OF THE BACKGROUND

Many cosmetic formulations are currently intended to be applied to skin: this is an intrinsic feature of beauty products, make-up products and body-care products. It is sought, very naturally, to thicken such formulations in a pH range matching that of skin, i.e., at values of between 5 and 7, and preferentially between 5 and 6.5, and very preferentially between 5.5 and 6.

There are a number of technical solutions to this problem, which may be classified into 4 categories: use of polymers of higher molecular weights and in powder form, the technique called "back-acid", which relies on acrylic polymers in direct emulsion of polymer particles in water, use of other polymers, again in the form of direct emulsions, and finally the use of reverse emulsions.

In the first category, one may cite document EP 1 138 703 A1, which describes a cosmetic topical composition, including a polymer of high molecular weight, with a base of at least one monomer having a free strong acid group copolymerised with at least one esterified monomer and terminated by a hydrophobic group having 8 to 30 carbon atoms.

The abovementioned polymer is an emulsifying polymer, in solid form; it can be dispersed in water and it enables the composition which contains it to be thickened, notably for pH values close to 5.

However, these polymers have the disadvantages relating to the use of a powder: difficulties of transport and cleaning, dangerousness of the product relating to its powdery, irritant and particular character. In addition, these polymers must be solubilised in the medium to be thickened, through the introduction of surfactants. The latter constitute additional formulation additives which make the formulation more complex, and which can interact with the surfactants already contained in the formulation, sometimes creating undesirable effects (notably phase separation, or the formation of residual insolubles).

The technique called "back-acid" is also known, as described in document WO 01/76 552. This is a method consisting in introducing a surfactant and an alkali-swellable acrylic copolymer into an aqueous medium. This leads to a thickening effect when its carboxylic acid groups are neutralised: a three-dimensional network is then created which leads to an increase of the viscosity of the aqueous phase. Such an effect may be activated in a pH area close to 6, the role of the surfactant being to maintain the thickening effect, even when the pH is reduced.

In addition to the abovementioned ion mechanism, there is an associative mechanism, based on the presence of a hydrophobic monomer: this is what is described by document WO 03/62 288, which also seeks to thicken formulations with an acidic pH. The same goes for document U.S. Pat. No. 4,529,773 A1. As with the back-acid method, the presence of a surfactant in the form of an additional product is therefore necessary, leading to the previously mentioned disadvantages.

A number of documents which describe the use of other polymers in emulsion are also known. In this respect, document EP 0 824 914 B1 describes a polymer containing an aminated cationic monomer. The sought thickening effect will be obtained with an acidic pH through ionisation of the aminated cationic monomer. In document WO 2004/024 779, the cationicity of the envisaged polymer is provided by a substituted amino vinylic monomer. With this ease also it is possible to thicken an aqueous medium with an acidic pH.

However, the toxicity of cationic polymers for aquatic fauna is well known: and they are unfortunately found at the life-cycle end in our rivers, both large and small, into which they are discharged through the domestic water system.

Finally, reverse emulsions and their applications as thickening agents in the cosmetics field are also known, as disclosed in documents WO 2004 063228 A1 and GB 2 422 605 A1. However, these structures require the presence of surfactants and solvents to ensure their stability, and the disadvantages mentioned above are then posed.

SUMMARY OF THE INVENTION

In continuing their research with a view to thickening aqueous compositions, notably with pHs of less than 7, whilst overcoming the disadvantages of the methods of the prior art, the inventors have developed a thickening method using original structures. These are direct emulsions in water of alkali-swellable (meth)acrylic polymers, three characteristics of which are:

absence of surfactants and organic solvents other than water, majority presence of acrylic acid compared to methacrylic acid, and the presence of a quantity of a particular monomer which is 2-acrylamido-2-methylpropane sulfonic acid (or AMPS, CAS n°: 40623-75-4).

These products advantageously enable a formulation to be thickened, without however introducing new surfactants, or organic solvents other than water, into the formulation. In addition, it is possible to activate the thickening phenomenon in a pH zone of between 5 and 7, without using the "back-acid" technique.

There was no knowledge of how to produce alkali-soluble emulsions which were rich in acrylic acid and free of surfactants and organic solvents other than water, before the importance of AMPS in such emulsions was discovered. It is the presence of a certain quantity of the latter which allows such products to be produced, with the previously mentioned attractions, which are particularly advantageous in the field of cosmetics, notably in order to thicken formulations with a pH of less than 7, notably between 5 and 6.5, and more preferentially between 5.5 and 6. These emulsions were described for the first time in French Patent Applications which have been filed as numbers FR 10 55080 and FR 10 55077, both incorporated herein by reference.

BRIEF DESCRIPTION OF THE FIGURE

FIG. 1 shows the results of tests where the change in the Brookfield™ viscosity in mPa·s of a gel (Y axis) was measured as a function of the pH (X axis).

DETAILED DESCRIPTION OF THE PREFERRED EMBODIMENTS

As used herein the expression "direct emulsion of a polymer in water" designates a stable and uniform dispersion of polymer particles in water (no reference is made here to emulsions of the oil-in-water or water-in-oil type, which imply the existence of two separate phases, one water-based and the other oil-based). Concerning the expression "alkali-swellable polymer", it signifies that the polymer is capable, when the medium is alkaline, of incorporating a quantity of water such that there is formation of a gel and therefore an increase of viscosity.

The emulsions referred to in the present invention cover two major families of thickening agents: those of the ASE type (Alkali-Swellable Emulsion) and those of the HASE type (Hydrophobically modified Alkali-Swellable Emulsion). The former designate copolymers of (meth)acrylic acid with a non-water-soluble ester of these acids, and the latter designate copolymers with a (meth)acrylic acid base of a non-water-soluble ester of (meth)acrylic acid and of a monomer having hydrophobic groups called "associative" groups. These copolymers can also be cross-linked.

The action mechanisms of these products, and notably the alkali-swellable character of these emulsions and their ability to thicken an aqueous medium with a pH close to neutrality, have been described in documents WO 2007/144721 and "Practical guide to associative thickeners" (Proceedings of the Annual Meeting Technical Program of the FSCT, 2000, 78th, 644-702), Thickening agents of the ASE and HASE type are generally manufactured in the form of direct emulsions of the alkali-swellable polymer in water, the active product content of which varies between 10% and 45% of their total weight.

The corresponding synthesis method is notably described in the following publications: "Synthesis of an alkali-swellable emulsion and its effect on the rate of polymer diffusion in poly(vinyl acetate-butyl acrylate) latex films" (Journal of Polymer Science, Part A: Polymer Chemistry, 2005, 43 (22), pp. 5632-5642), "Structural and rheological properties of hydrophobically modified alkali-soluble emulsion solutions" (Journal of Polymer Science, Part B: Polymer Physics, 2002, 40(18), pp. 1985-1994). It is also the subject of many patent applications (EP 0 089 213 A1, EP 0 646 606 A1, EP 0 979 833 A1 in respect of ASEs and EP 0 013 836 A1, WO 93/2454 A1, U.S. Pat. No. 4,268,641 A1, U.S. Pat. No. 4,421,902 A1 U.S. Pat. No. 3,915,921 A1 in respect of HASEs).

One object of the present invention is a method for thickening a cosmetic formulation, through contact of the formulation with a direct aqueous emulsion of a polymer, followed by regulation of the pH to a value between 5 and 7, preferentially between 5 and 6.5, and very preferentially between 5.5 and 6, wherein the emulsion is free from surfactants and organic solvents other than water, and in that the polymer comprises, consists essentially of, or consists of, expressed as a % by weight of each of the monomers:
  a) 20% to 60% by weight of methacrylic acid and acrylic acid,
  b) 40% to 80% by weight of at least one monomer chosen from among ethyl acrylate, butyl acrylate, methyl methacrylate and their blends,
  c) 0.05% to 22% by weight of 2-acrylamido-2-methyl-propane sulfonic acid,
  d) 0 to 1% by weight of at least one cross-linked monomer, where the total a)+b)+c)+d) equals 100%,
or
  a) 20% to 60% by weight of methacrylic acid and acrylic acid,
  b) 40% to 80% by weight of at least one monomer chosen from among ethyl acrylate, butyl acrylate, methyl methacrylate and their blends,
  c) 0.5% to 25% by weight of a monomer containing a hydrophobic group,
  d) 0.05% to 22% by weight of 2-acrylamido-2-methyl-propane sulfonic acid,
  e) 0 to 1% by weight of at least one cross-linked monomer, where the total a)+b)+c)+d)+e) equals 100%,
where in both cases the % by weight of acrylic acid compared to the total weight of the acrylic and methacrylic acids is between 50% and 100%, preferentially between 80% and 100%, very preferentially between 98% and 100%, and extremely preferentially where this % equals 100% (there is thus no methacrylic acid).

The first type of composition indicated above is an emulsion of the ASE type which is rich in acrylic acid, and the second is an emulsion of the HASE type which is rich in acrylic acid.

In the polymers of the invention it is understood that the monomers that make up the polymers exist in polymerized form, but they are nevertheless commonly referred to as polymers containing monomers, in accord with convention.

In the invention method a preferred embodiment is wherein the monomer containing a hydrophobic group has the general formula R-(OE)$_m$-(OP)$_n$-R', where:
  m and n designate integers of less than or equal to 150, at least one of which is non-zero,
  OE and OP designate respectively ethylene oxide and propylene oxide,
  R designates a polymerisable group, and preferentially the methacrylate or methacrylurethane group,
  R' designates a hydrophobic group having at least 6 and at most 36 carbon atoms.

In the invention method a preferred embodiment is wherein the cross-linked monomer is chosen from among ethylene glycol dimethacrylate, trimethylolpropanetriacrylate, diallyl phtalate, allyl acrylate, the allyl maleates, methylene-bis-acrylamide, methylene-bis-methacrylamide, tetrallyloxyethane, the triallylcyanurates, the allylic ethers and the acrylic, methacrylic and methacrylurethane esters obtained from polyols.

In the invention method a preferred embodiment is wherein the aqueous emulsion has a dry extract of between 10% and 50% by dry weight of polymer, compared to its total weight.

In the invention method a preferred embodiment is wherein the emulsion has a particle size of between 50 nm and 500 nm.

In the invention method a preferred embodiment is wherein the polymer has an average molar mass by weight of between 20,000 Oriole and 1,000,000 g/mole.

In the invention method a preferred embodiment is wherein the formulation, preferably a cosmetic formulation, is chosen from among the forms containing at least one surfactant, and notably from among those intended to be applied to skin (care creams, make-up products, foaming agents, shampoos, etc.).

The following examples allow the invention to be better understood, without however limiting its scope.

EXAMPLES

Example 1

This example relates to the thickening of water at a pH of 5.5.

3 emulsions of the HASE type according to the invention, using a polymer the mass composition of which is given in table 1, were tested.

TABLE 1

| Test n° | AA | AMA | AE | Methacrylate $C_{22}(OE)_{25}$ | AMPS |
|---|---|---|---|---|---|
| 1 | 35.7 | 0.6 | 52.5 | 10 | 1.2 |
| 2 | 44.2 | 0.3 | 49.35 | 4.95 | 1.2 |
| 3 | 38.40 | 0.3 | 55.2 | 4.9 | 1.2 |

AA: acrylic acid
AMA: methacrylic acid
AE: ethyl acrylate
Methacrylate $C_{22}(OE)_{25}$: a monomer of general formula R—(OE)$_m$—(OP)$_n$—R', where m = 25, n = 0, OE and OP designate respectively ethylene oxide and propylene oxide, R designates the methacrylate group, and R' designates the linear alkyl group having 22 carbon atoms
AMPS: 2-acrylamido-2-methylpropane sulfonic acid In the course of test n° 4 a polymer sold by the company Lubrizol™ under the name Aqua SF-1 was also used.

For each test, 1% by dry weight of the polymer for testing, compared to the total weight of water to be thickened, was used. The change in the Brookfield™ viscosity in mPa·s of the gel, measured at 100 revolutions per minute and at 25° C., was measured, as a function of the pH which was increased through the gradual addition of sodium hydroxide.

FIG. 1/1 shows this change in the case of tests n° 1 (lozenges), 2 (squares), 3 crosses) and 4 (circles).

It can be seen clearly that the method according to the invention which uses the emulsions with AMPS enables the thickening phenomenon to be activated for much lower pH values than with the commercial polymer.

In addition, the thickening power in the pH zone between 5.5 and 6 is greater in the case of the polymers of the invention than for the polymer of the prior art.

In view of the above, a preferred embodiment of the invention herein is a method for thickening a formulation, comprising contacting the formulation with a direct aqueous emulsion of a polymer to form a thickened formulation, followed by regulation of the pH of the thickened formulation to a value between 5 and 7, wherein the emulsion is free from surfactants and organic solvents other than water and the polymer consists, expressed as a % by weight of each of the monomers therein, of:
a) 20% to 60% by weight of methacrylic acid and, optionally, acrylic acid where the % by weight of acrylic acid compared to the total weight of acrylic and methacrylic acid is at least 50%,
b) 40% to 80% by weight of at least one monomer chosen from among ethyl acrylate, butyl acrylate, and methyl methacrylate,
c) (105% to 22% by weight of 2-acrylamido-2-methylpropane sulfonic acid, and
d) 0 to 1% by weight of at least one cross-linked monomer,
or
a) 20% to 60% by weight of methacrylic acid and, optionally acrylic acid, where the % by weight of acrylic acid compared to the total weight of acrylic acid and methacrylic acid is at least 50%,
b) 40% to 80% by weight of at least one monomer chosen from among ethyl acrylate, butyl acrylate, and methyl methacrylate,
c) 0.5% to 25% by weight of a monomer comprising a hydrophobic group,
d) 0.05% to 22% by weight of 2-acrylamido-2-methylpropane sulfonic acid, and
e) 0 to 1% by weight of at least one cross-linked monomer.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for thickening a formulation, the method comprising:
   contacting the formulation with a direct aqueous emulsion of a polymer, followed by
   regulating a pH of the formulation to a value between 5 and 7, thereby forming a thickened formulation,
   wherein the emulsion is free from surfactants and organic solvents other than water and
   the polymer consists, expressed as a content by weight of monomers therein, of:
   a) from 20% to 60% by weight of acrylic acid and, optionally, methacrylic acid, wherein a content by weight of acrylic acid compared to a total weight of acrylic and methacrylic acid is at least 50%,
   b) from 40% to 80% by weight of ethyl acrylate, butyl acrylate, methyl methacrylate, or any combination thereof,
   c) from 0.05% to 22% by weight of 2-acrylamido-2-methylpropane sulfonic acid, and
   d) from 0 to 1% by weight of at least one cross-linked monomer.

2. The method according to claim 1, wherein the cross-linked monomer is present and is ethylene glycol dimethacrylate, trimethylolpropanetriacrylate, diallyl phtalate, allyl acrylate, an allyl maleate, methylene-bis-acrylamide, methylene-bis-methacrylamide, tetraallyloxyethane, a triallylcyanurate, an allylic ether, an acrylic ester obtained from a polyol, a methacrylic ester obtained from a polyol, a methacrylurethane ester obtained from a polyol, or any combination thereof.

3. The method according to claim 1, wherein the aqueous emulsion has a dry extract of between 10% and 50% by dry weight of polymer, compared to its total weight.

4. The method according to claim 1, wherein the emulsion has a particle size of between 50 nm and 500 nm.

5. The method according to claim 1, wherein the polymer has an average molar mass by weight of between 20,000 g/mole and 1,000,000 g/mole.

6. The method according to claim 1, wherein the content by weight of acrylic acid compared to the total weight of the acrylic acid and methacrylic acid is from 80% to 100%.

7. The method according to claim 1, wherein the content by weight of acrylic acid compared to the total weight of the acrylic acid and methacrylic acid is from 98% to 100%.

8. The method according to claim 1, wherein the polymer does not comprise methacrylic acid.

9. The method according to claim 1, wherein the formulation is a cosmetic formulation.

10. The method according to claim 9, wherein the cosmetic formulation comprises a surfactant and is suitable for application to human skin.

11. The method according to claim 1, wherein the formulation has a pH of from 5 to 6.5 after thickening.

12. The method according to claim 8, wherein the formulation has a pH of from 5.5 to 6 after thickening.

13. The method according to claim 1, wherein the 40% to 80% by weight of (b) is a combination of two monomers selected from the group consisting of ethyl acrylate, butyl acrylate, and methyl methacrylate, or else is a combination of ethyl acrylate, butyl acrylate, and methyl methacrylate.

14. The method according to claim 1, wherein, for a 1% dry weight content of the polymer in the thickened formulation, a viscosity of the thickened formulation is at least 1200 mPas at a pH of 7.

15. The method according to claim 1, wherein, for a 1% dry weight content of the polymer in the thickened formulation, a viscosity of the thickened formulation is at least 400 mPas greater at a pH of 6 than at a pH of 5.

16. The method according to claim 1, wherein, for a 1% dry weight content of the polymer in the thickened formulation, a viscosity of the thickened formulation is at least 1200 mPa·s greater at a pH of 7 than at a pH of 5.

17. The method according to claim 15, wherein, for a 1% dry weight content of the polymer in the thickened formulation, a viscosity of the thickened formulation is at least 1200 mPa·s greater at a pH of 7 than at a pH of 5.

18. The method according to claim 1, wherein:
   the emulsion has a particle size of between 50 nm and 500 nm, and
   the polymer has an average molar mass by weight of between 20,000 g/mole and 1,000,000 g/mole.

19. The method according to claim 18, wherein the content by weight of acrylic acid compared to the total weight of the acrylic acid and methacrylic acid is from 80% to 100%.

20. The method according to claim 19, wherein the cross-linked monomer is present and is ethylene glycol dimethacrylate, trimethylolpropanetriacrylate, diallyl phtalate, allyl acrylate, an allyl maleate, methylene-bis-acrylamide, methylene-bis-methacrylamide, tetraallyloxyethane, a triallylcyanurate, an allylic ether, an acrylic ester obtained from a polyol, a methacrylic ester obtained from a polyol, a methacrylurethane ester obtained from a polyol, or any combination thereof.

* * * * *